(12) United States Patent
Kim et al.

(10) Patent No.: US 8,320,718 B2
(45) Date of Patent: Nov. 27, 2012

(54) OPTICAL SENSORS AND METHODS OF MAKING THE SAME

(75) Inventors: Sora Kim, Niskayuna, NY (US); Faisal Razi Ahmad, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 144 days.

(21) Appl. No.: 12/795,037

(22) Filed: Jun. 7, 2010

(65) Prior Publication Data
US 2011/0299807 A1  Dec. 8, 2011

(51) Int. Cl.
*G02B 6/00* (2006.01)
*G02B 6/26* (2006.01)
*G02B 6/42* (2006.01)

(52) U.S. Cl. .......................................... 385/12; 385/27
(58) Field of Classification Search .................... 385/12, 385/27
See application file for complete search history.

(56) References Cited

U.S. PATENT DOCUMENTS

| 7,512,298 | B2 | 3/2009 | Yi et al. |
| 2004/0120638 | A1* | 6/2004 | Frick .............................. 385/27 |
| 2008/0265147 | A1* | 10/2008 | Fan et al. ................. 250/227.24 |
| 2009/0208209 | A1 | 8/2009 | Ng et al. |
| 2009/0310902 | A1* | 12/2009 | Smith et al. ..................... 385/12 |

OTHER PUBLICATIONS

Michiel Vanhoutte; "Biosensors based on circular resonators with vertical outcoupling structures"; http://www.photonics.intec.ugent.be/download/mth_29.pdf; 103 Pages.

* cited by examiner

*Primary Examiner* — Brian M. Healy
*Assistant Examiner* — Mary El Shammaa
(74) *Attorney, Agent, or Firm* — Paul J. DiConza

(57) ABSTRACT

A sensor is provided. The sensor includes a substrate, a waveguide having a first surface and a second surface, wherein the waveguide is disposed on the substrate such that at least a portion of the second surface of the waveguide is in physical contact with the substrate, a holder component disposed on at least a portion of the substrate, or the waveguide, or both, wherein the holder component comprises one or more cavities. The sensor further includes at least one microsphere at least partially disposed in a corresponding cavity of the holder component.

21 Claims, 9 Drawing Sheets

OPTICAL SENSORS AND METHODS OF MAKING THE SAME

BACKGROUND

The invention relates generally to sensors, and particularly to optical sensors and methods of making the same.

In recent times, there has been an increasing demand for optical sensors that can detect small amounts of analytes, such as proteins, DNA, toxins, and biological pathogens. Optical sensors based on microspheres have been used to detect the presence and/or concentration of small particles. Typically, in a microsphere based optical sensor, an optical fiber evanescently couples light to a microsphere. To assist in coupling light from the fiber into microsphere, the region of the fiber that is in close proximity to the micro sphere is tapered. The tapered end is aligned with the microsphere. An evanescent electromagnetic field associated with total internal reflection exists just outside the microsphere. This electromagnetic field decays exponentially as a function of distance, typically over a distance in a range from about 0.1 to 0.3 microns. The evanescent field is affected by changes in the surface properties of the microsphere, which in turn is influenced by the environment of the microsphere. The existing microsphere based optical sensors require high degrees of precision control of a gap between the tapered optical fiber end and the microsphere to achieve the optimal coupling efficiency.

Increasing the number of microspheres in a system has several commercial benefits such as multi-channel detection and higher throughput for bio-assay analysis. The existing coupling method translates into a limit on flexibility of expanding the applications of such optical sensors to larger systems, such as chip-scale sensors, and portable sensors. For example, as the number of microspheres increases, the complexity of the fiber alignment increases exponentially. In addition to the increasing complexity, positioning the microspheres having different sizes at the optimal locations and fixing the locations of the micro spheres is also challenging.

In addition to increasing the throughput, it is desirable to enhance the sensitivity of such optical sensors. For example, enhanced sensitivity may enable detection of individual protein molecules, or virus particle detection of extremely low concentration exposures that might otherwise go unnoticed, earlier warnings to exposures, a greater area of overall coverage with fewer sensors, to name a few.

Therefore, there is a need for an improved sensor that employs an effective and efficient way for coupling light to an optical resonator, which comprises one or more microspheres. Further, there is a need for sensor design that enables multi-channel detection for high throughput.

BRIEF DESCRIPTION

In one embodiment, a sensor is provided. The sensor includes a substrate, a waveguide having a first surface and a second surface, wherein the waveguide is disposed on the substrate such that at least a portion of the second surface of the waveguide is in physical contact with the substrate, a holder component disposed on at least a portion of the substrate, or the waveguide, or both, wherein the holder component comprises one or more cavities. The sensor further includes at least one microsphere at least partially disposed in a corresponding cavity of the holder component.

In another embodiment a sensor system is provided. The sensor system includes a light source, a sensor disposed to receive illumination from the light source, and a detector that detects a shift in a resonance wavelength of one or more microspheres of the sensor. The sensor includes a substrate, a waveguide having a first surface and a second surface, wherein the waveguide is disposed on the substrate such that at least a portion of the second surface of the waveguide is in physical contact with the substrate, a holder component disposed on at least a portion of the substrate, or the waveguide, or both, wherein the holder component comprises one or more cavities, and at least one microsphere at least partially disposed in a corresponding cavity of the holder component.

In yet another embodiment, a method for making a sensor is provided. The method includes providing a waveguide disposed on a substrate, disposing a holder component on at least a portion of the substrate, or the waveguide, or both, wherein the holder component comprises at least one cavity, and disposing at least one microsphere in the at least one cavity of the holder component.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
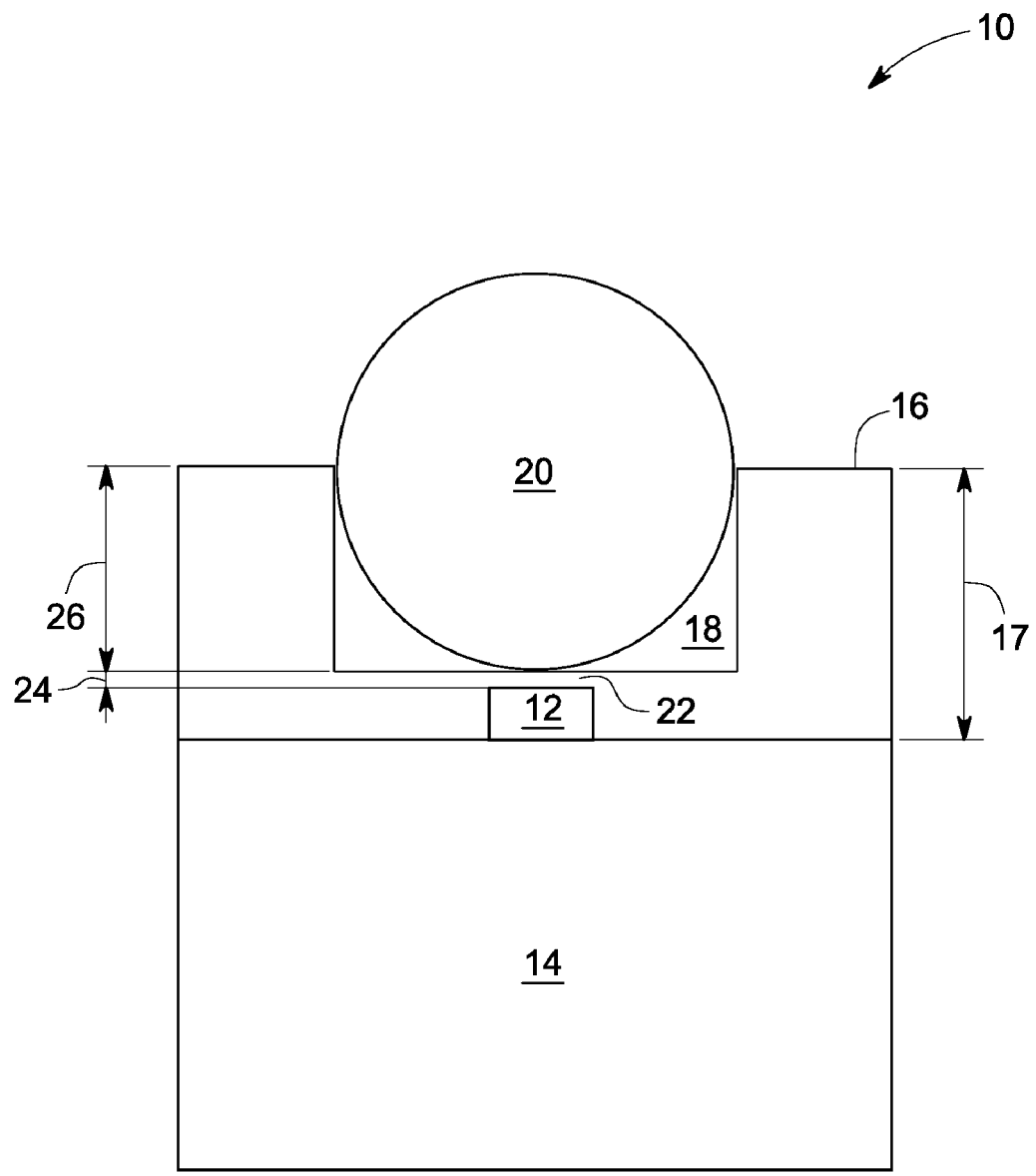
FIG. 1-4 are cross-sectional views of examples of optical sensors using a single microsphere, in accordance with embodiments of the present technique.

Embodiments of the present invention include optical sensors for detecting the presence of, identifying the composition of, and/or measuring an amount or concentration of substances, such as chemical or biological entities. In certain embodiments, the sensors may be used for detection of amounts as small as single proteins or virus particles. The analytes may be present either in a liquid medium or a gaseous medium. For example, the analytes may be present in a liquid solution, or may be air-borne molecules. As used herein, the term "concentration" of an analyte includes instances in which the sample does not contain any analyte (zero amount) to instances in which the sample contain up to any infinite amount of the analyte in the solution. For example, if the sample solution does not include any of the analyte, the "concentration" of the analyte in the solution will be zero. In certain embodiments, the sensor is provided for simultaneous detection of concentration of two or more different analytes in a solution, or a concentration of a single analyte from two or more different solutions. The sensor may also be used to detect the rate of reaction of the analytes reacting with their corresponding anti-bodies or binding agents in the solution.

In certain embodiments, the sensor may detect and/or measure a chemical substance using a change in one or more properties of photons orbiting within a microsphere. Generally, resonances in geometrical optics are associated with optical ray paths. When a light enters a microsphere, total internal reflection keeps the photon(s) from radiating outward from the microsphere. Typically, the light circles (or orbits) the interior of the micro sphere, returning in phase after a roundtrip within the circle. This is known as a mode of the first order. For higher order modes, the photon(s) takes several orbits before the ray path closes—i.e., before the photon returns in phase. Each microsphere has an associated resonance frequency at which the light is confined in one of the many optical modes of the microsphere geometry. Any change in one or more of the size, shape, or refractive index of the micro sphere results in a shift in the optical resonance frequency of the microsphere. For example, when employing the microspheres in a sensor, a binding event may cause a change in property of the surface of the microsphere. For example, if binding of the analyte results in an increase in the diameter of the micro sphere, the resonance frequency shifts towards longer wavelengths.

In certain embodiments, the sensor includes a substrate, and a waveguide having a first surface and a second surface. The waveguide is disposed on the substrate such that at least a portion of the second surface of the waveguide is in physical contact with the substrate. As used herein, 'disposed on' refers to an arrangement where either a first surface is in direct physical contact with a second surface, or one or more intervening layers may be present between the first and the second surfaces and the surfaces are associated with each other by an indirect contact. Further, the sensor includes a holder component disposed on at least a portion of the substrate, or the waveguide, or both. The holder component includes one or more cavities, such that at least one microsphere is at least partially disposed in a corresponding cavity of the holder component. In one example, a functional material (receptor for an analyte) may be disposed on the microsphere.

In certain embodiments, the substrate may include one or more of a semiconductor, a ceramic, a polymer, or a metal. The substrate may be a patterned structure or a continuous structure. It should be noted that the term "substrate" refers to a bulk material, or a bulk material having one or more layers disposed on the bulk material. In one example, the substrate may be a silicon wafer. In another example, the substrate may be a silicon-on-insulator (SOI) wafer. The dimensions (e.g., thickness) of the substrate may be chosen so as to provide mechanical stability to the sensor structure.

As used here, the term "waveguide" encompasses a structure that enables guidance and propagation of a light wave. In certain embodiments, the waveguide may include a single mode waveguide, a multiple-mode waveguide, a rectangular waveguide, a slot waveguide, or combinations thereof. In one embodiment, the waveguide may be an optical fiber. Non-limiting choices for materials for waveguides may include inorganic glasses (such as silica, alumina), silicon, III-V compound semiconductors, II-VI compound semiconductors, a polymer, or other known materials for optical fibers and waveguides. In one example, the polymer may include an amorphous polymer, such as poly(methyl methacrylate) (PMMA).

In some embodiments, the holder component includes a continuous layer. For example, the holder component may include a thin film having one or more cavities of desired shape and/or size. In other embodiments, the holder component is made of a plurality of discrete portions comprising one or more cavities. In one example, each of the discrete portions may include one or more cavities for disposing the microspheres. The discrete portions may have same or different sizes. In one example, the size of the discrete portions may be proportional to the size of the microspheres that need to be disposed in the cavities of the discrete portions. In another embodiment, all the discrete portions may have same size.

The size of the cavity may be such that a corresponding micro sphere is at least partially disposed within the cavity. In one example, the micro sphere may be completely disposed within the cavity. The micro sphere disposed in the cavity may be in contact with a bottom portion of the cavity disposed above the waveguide. Alternatively, the micro sphere may be in direct physical contact with the first surface of the waveguide. The relative position of the microsphere and the waveguide may be determined so as to provide optimum optical coupling between the waveguide and the microsphere. Depending on the ease of fabrication and other factors (such as the material of the holder component, and the method employed to form the cavities), the cavities may have any desired shape, such as, but not limited to, a cylindrical shape, a trapezoidal shape, and a tapered shape. In addition, the cross-sectional area of the cavities may have different shapes, such as a circular shape, an elliptical shape, a square shape, a rectangular shape, or any other geometrical or irregular shape. The dimensions of the cavity, including the depth of the cavity, and the diameter of the cross-sectional area of the cavity may be chosen so as to enable the micro sphere to be held in place within the cavity. The depth of the cavity is sized to receive the corresponding micro sphere. Also, the depth of the cavity is such that it is sufficient to retain the microsphere. As used herein, the term "diameter" refers to a distance between two farthest points along a periphery of the cavity. For example, in case of a polygon, the diameter is the largest distance between any pair of vertices. In other words, the diameter is the length of the longest polygon diagonal (e.g., straight line segment joining two vertices).

In certain embodiments, the holder component includes a plurality of cavities. In one embodiment, only some of the cavities may have microspheres disposed in them, the other cavities may be empty. In another embodiment, all the cavities may have corresponding microspheres. The number of microspheres employed may depend on the number and/or types of analytes to be detected.

In certain embodiments, a thickness of the holder component may be in a range from about 500 nanometers to about 500 microns. The thickness of the holder component may be determined based on a size of the microspheres, and a thickness of the portion of the holder component desired between the first surface of the waveguide and the microsphere for optimum optical coupling between the waveguide and the holder component. The distance between the microsphere and the waveguide may affect the performance of the sensor. More specifically, if the microsphere and waveguide are too far apart, the optical coupling of their respective evanescent fields may be insufficient. On the other hand, if the microsphere and waveguide are too close, the presences of the waveguide's evanescent field may change the boundary condition of the microsphere, thereby undermining the inherently high quality factor (Q) of the resonance. In one example, the microsphere may be in physical contact with the waveguide. In this example, the holder component may not be present on at least a portion of the upper surface of the waveguide. In one embodiment, the thickness of the portion of the holder component disposed between the first surface of the waveguide and the microsphere may be in a range from about 0 micron to about 2 microns. The distance between the waveguide and the microspheres may be adjusted by adjusting the size and shape of the cavities.

In certain embodiments, the first surface of the waveguide and the at least one microsphere are spaced apart from each other to define a gap. The gap may include air, gas (e.g., inert gas), or other suitable medium. Again, in instances where a gas is present in the gap between the waveguide and the microsphere, the gas (or a combination of gases) may be chosen such that the refractive index of the material of the holder component is less than the individual refractive indices of the materials of the waveguide and the microsphere. Suitable gases may include, but are not limited to, nitrogen, xenon, or argon.

The material of the holder component is chosen to enable efficient optical coupling between the waveguide and the microsphere. In one embodiment, holder component may be made of a dielectric material, a thermally curable polymer (e.g., a ultraviolet curable polymer), an insulator material, such as, but not limited to, glass, plastic, or aerogel, PMMA or polymer depending on the materials of waveguides and micro spheres.

The microsphere(s) may be made of any transparent material, such as silicon, silica, sapphire, polystyrene, PMMA, polycarbonate, poly(ethylene terephthalate), or the like. Microspheres of different diameters are commercially available. In certain embodiments, a diameter of the microsphere may be in a range from about 1 micron to about 1 millimeter. The diameter of the microsphere may be selected based on the type of analyte to be detected. For example, for bovine serum albumin (BSA) as an analyte, the diameter of the microsphere may be in a range from about 10 microns to about 100 microns.

In certain embodiments, the waveguide may be coupled to two or more microspheres. Advantageously, such an arrangement provides for analysis of two or more analytes simultaneously. In one embodiment, the sensor may include a plurality of uniquely sized microspheres to detect different analytes. In one embodiment, a difference in diameters of any two micro spheres is at least about two percent of the diameter of the smaller microsphere.

It is desirable to keep the refractive indices of the microsphere(s) and the waveguide close to each other to optimize optical coupling, or in other words, to enhance evanescent connection between the microspheres and the waveguide. In some embodiments, the microsphere(s) and the waveguide may be made of same material.

In certain embodiments, the sensitivity of the sensor may be increased by reducing the size of the micro sphere, or using a material with higher refractive index to form the microspheres.

In one embodiment, the microspheres may include a modifier material disposed on at least one microsphere. In instances where the material of the microspheres is different from the material of the waveguide, and if the difference in refractive indices of the material of the waveguide and the microsphere may not allow for an optimized optical coupling between the micro sphere and the waveguide, the modifier material may be used to reduce or eliminate the difference between the refractive indices of the waveguide and the microsphere. In one example, the microsphere may be coated with a modifier material that has a refractive index that matches the refractive index of the waveguide. In one example, the material of the waveguide and the modifier material may be the same. In one example, the microsphere may be made of glass, the waveguide may be made of silicon.

In this example, the modifier material may include poly-silicon, cadmium sulfide, cadmium selenide, various chalcogenide, chalcopyrite, II-VI semiconductors, or combinations thereof.

The modifier material may be disposed on the microsphere in the form of a layer. In one embodiment, the thickness of the layer of the modifier material may be in a range from about several tens of nanometer to about several tens of microns. The thickness of the modifier material may be maintained at a minimum so as to prevent any undesired effects on optical coupling between the waveguide and the microsphere. It may be noted that the modifier material may form a shell around the microsphere, and the optical mode may be guided in the shell formed by the modifier material. Suitable examples of the modifier material include a dielectric material, glass, silicon, poly-silicon, cadmium sulfide, cadmium selenide, various chalcogenide, chalcopyrite, II-VI semiconductors, or combinations thereof.

To adsorb target analytes, proteins, and chemicals and/or to avoid adsorption of any other chemicals, the surface of the one or more microspheres may include a functional material. The particular substance to be detected and/or measured may affect the design (e.g., size, material, etc.) of the microsphere, as well as the choice of the receptors (functional material). The functional material may be used to detect analytes by acting as a receptor for the analytes to bind the analytes to the surface of the microspheres. The receptor used depends upon the particular application for which the sensor is to be used. In one example, for covalently bonded microspheres, surface amines may be used as functional material to react to attach receptors. The functional material may be disposed on the microspheres in the form of a coating. In certain embodiments, the coating of the functional material may have a thickness of about 1 micron or less. The thickness of the functional material layer may be selected so as to enable optimum optical coupling between the micro sphere and the waveguide.

In one embodiment, the functional materials may irreversibly couple to the analytes. In another embodiment, the functional materials may couple reversibly to the analytes. Reversibility is desired if the sensors are to be re-used, however, reversibility may not be desired if the sensors are intended for one time use or are disposable.

In certain embodiments, the surface density of adsorption sites (provided by the functional material) may be increased by a factor of ten or more by using polymer brushes or gels disposed (for example, grown) on the surface of the microspheres. Ligands may be covalently bonded through many points on the brushes or gels. For instance, chlorosilane-containing initiator for surface polymerization may be used.

Other modifications of the microspheres are also envisioned. For example, the microspheres may be modified to minimize false signals by non-target chemicals that may be adsorbed onto the surface of the microspheres.

As mentioned above, the analytes (target molecules) may be present either in a liquid medium, or a gaseous medium. In the case of analytes being present in a gaseous medium (air-borne), the micro spheres may be simply exposed to the environment where the air-borne particles are to be detected. In case of analytes being present in the liquid medium, the micro spheres may be coupled to devices, such as microfluidic devices, that can transport the analyte solution to the functionalized or non-functionalized microspheres. In one example, the microfluidic device may include a plurality of channels. In this example, the two or more channels of the microfluidic device may be coupled to corresponding microspheres of the sensor. The microfluidic channels may include similar or different analyte solutions. In one example, where the various microfluidic channels include the same analyte solution, the different microspheres coupled to the microfluidic channels may be used to detect different analytes present in the analyte solution. In another example, where the microfluidic channels include different analyte solutions, the different microspheres may be coupled to corresponding microfluidic channels based on the analytes to be detected in the different microfluidic channels.

The sensor may be adapted for detecting analytes in the liquid or gaseous medium. In case of the analyte being present in the liquid medium, the micro spheres or the sensor may be disposed in a packaging. In this case, the microfluidic device may also be disposed within the packaging. In case of the analyte being present in the gaseous medium, for example, air-borne toxins, the micro spheres may not be disposed in a packaging as the surface of the micro spheres are desired to be exposed to the gaseous medium. In certain embodiments, the system may be configured for real time monitoring, such as, but not limited to, monitoring eluting species in a separation technique.

FIG. 1 illustrates a sensor 10 having a waveguide 12 disposed on a substrate 14. A holder component is disposed on the waveguide 12 and the substrate 14. In the illustrated embodiment, the holder component is a patterned layer 16. The patterned layer 16 includes a cavity 18 to receive the micro sphere 20. The patterned layer 16 may have a thickness 17 in a range from about 500 nanometers to about 150 microns. A portion 22 of the patterned layer 16 disposed between the micro sphere 20 and the cavity 18 may have a thickness 24 in a range from about zero to about several microns. In the illustrated embodiment, the cavity 18 may have a depth 26 in a range from about 500 nanometers to about 150 microns. The cavity 18 may have any geometrical shape as a cross-sectional area. Alternatively, the cavity 18 may have an irregular shape as the cross-sectional area.

Figure 2:
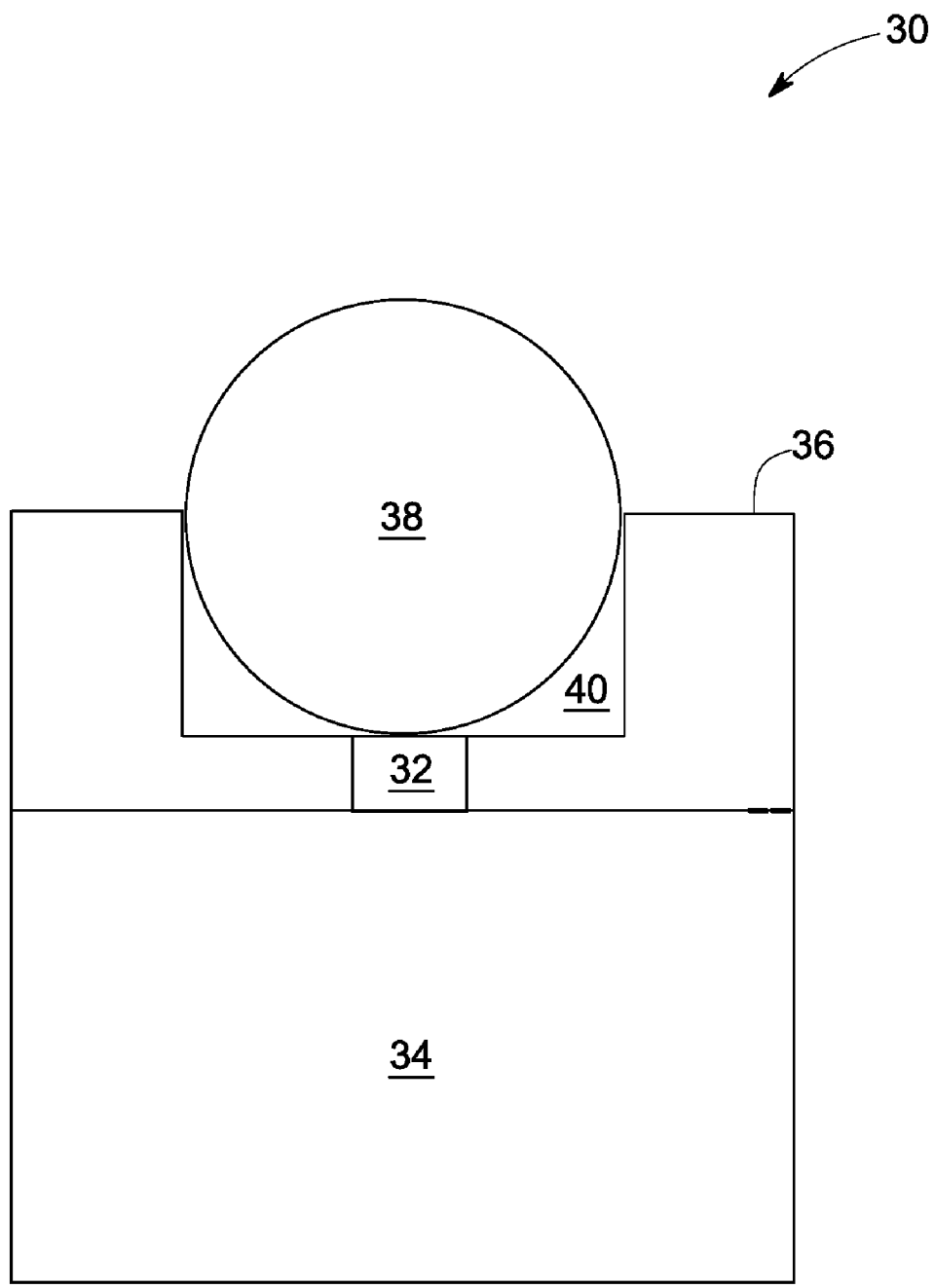

FIG. 2 illustrates a sensor 30 having a waveguide 32 disposed on a substrate 34. A holder component 36 is disposed on the substrate 34. In the illustrated component, the holder component 36 is not present on the waveguide 32. Accordingly, when the microsphere 38 is disposed in the cavity 40, the microsphere 38 comes in physical contact with the waveguide 32. In some instances, a direct physical contact may be desired for optimum optical coupling between the waveguide 32 and the micro sphere 38.

Figure 3:
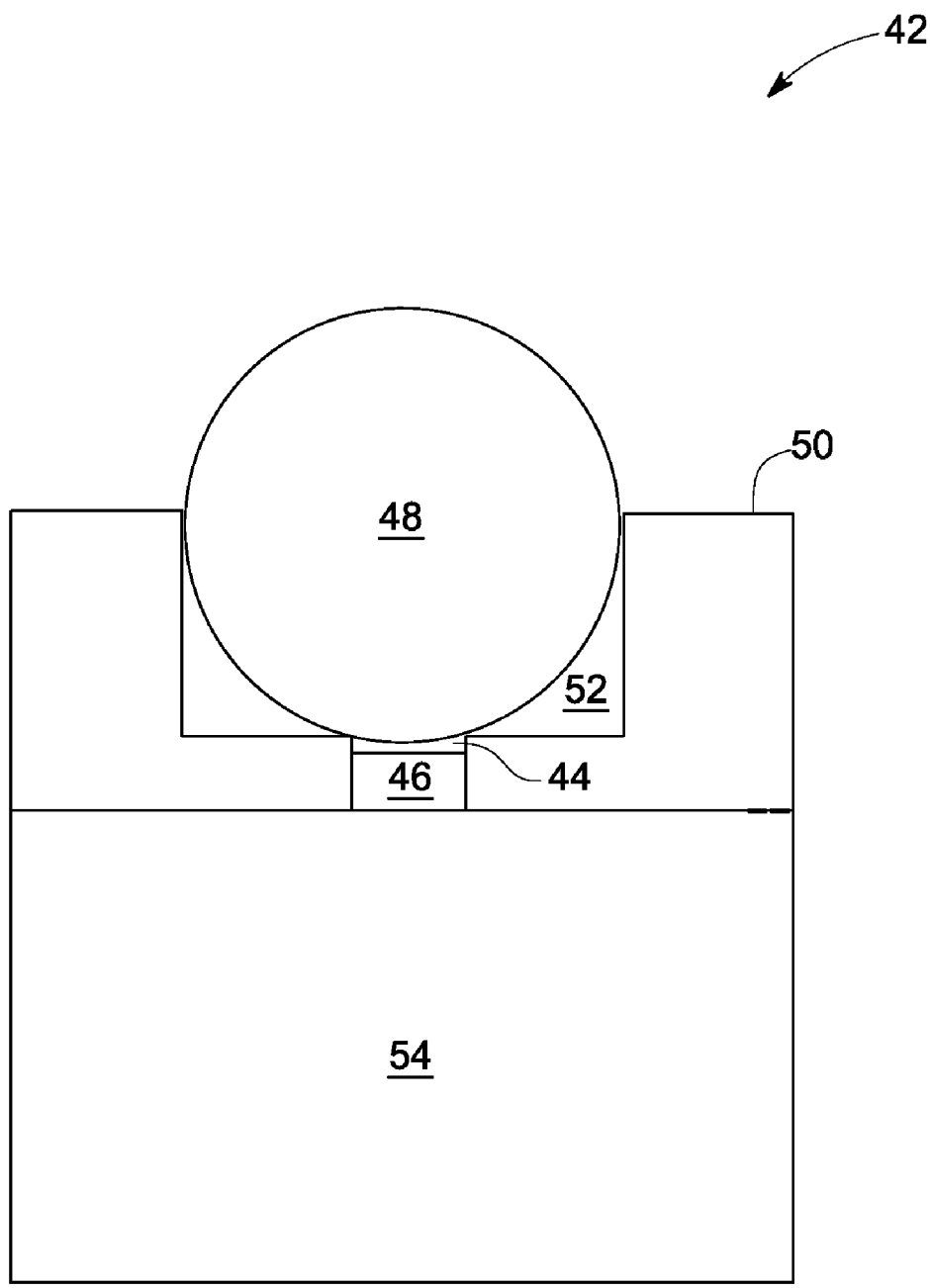

FIG. 3 illustrates a sensor 42 having a gap 44 disposed between the waveguide 46 and the microsphere 48. The gap 44 is part of the holder component 50. The gap 44 may be filled with air. The holder component 50 also includes a cavity 52 for disposing the microsphere 48. The holder component 50 is disposed partly on the substrate 54 and partly on the waveguide 46. The presence of gap 44 enables the use of air between the microsphere and the waveguide. The refractive index of materials disposed within the gap 44 needs to be smaller than the refractive indices of the microsphere 48 and the waveguide 44. In instances where the microsphere 48 and the waveguide 46 are made of materials with relatively low refractive indices, such as polymer or glass, it may be desirable to fill the gap 44 with air.

Figure 4:
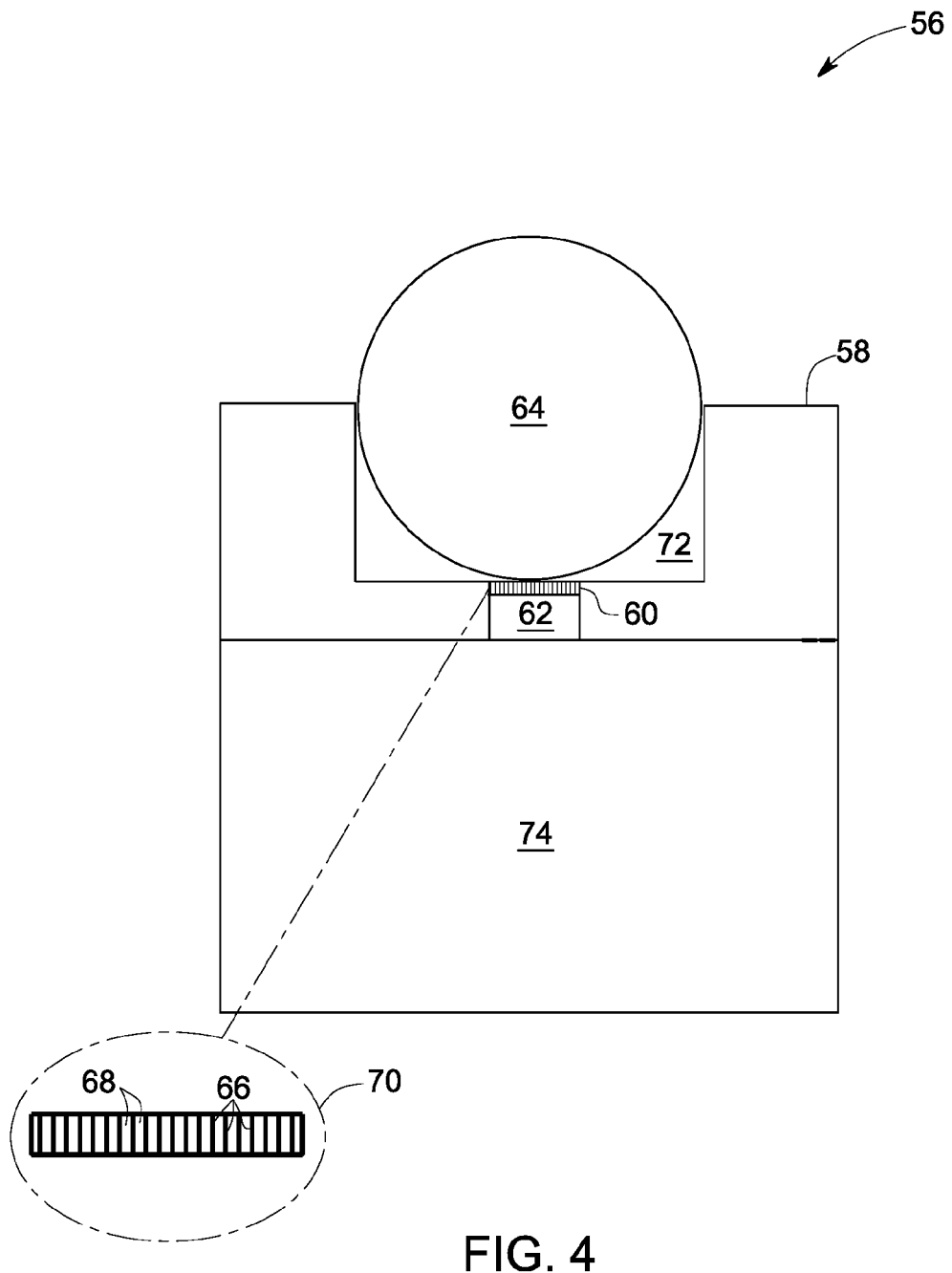

FIG. 4 illustrates a sensor 56 that includes holder component 58 having a patterned portion 60. The patterned portion 60 is disposed between the waveguide 62 and the microsphere 64. In one example, the patterned portion 60 may include an arrangement having alternatingly disposed columns 66 and 68 of the material of the holder component and air, respectively as illustrated in the enlarged view 70. Optimally designed pattern 60, such as 1D gratings or photonic crystals, may enhance the vertical coupling through resonances. Furthermore, in case of the materials of the patterned portions 60 having similar refractive index as that of the microsphere 64 and the waveguide 62, the effective refractive index of the patterned portion 60 may be lower depending on the fill factor of the periodic patterns (columns 66) of the patterned portion 60. The holder component 58 defines a cavity 72 and is disposed on a substrate 74.

Figure 5:
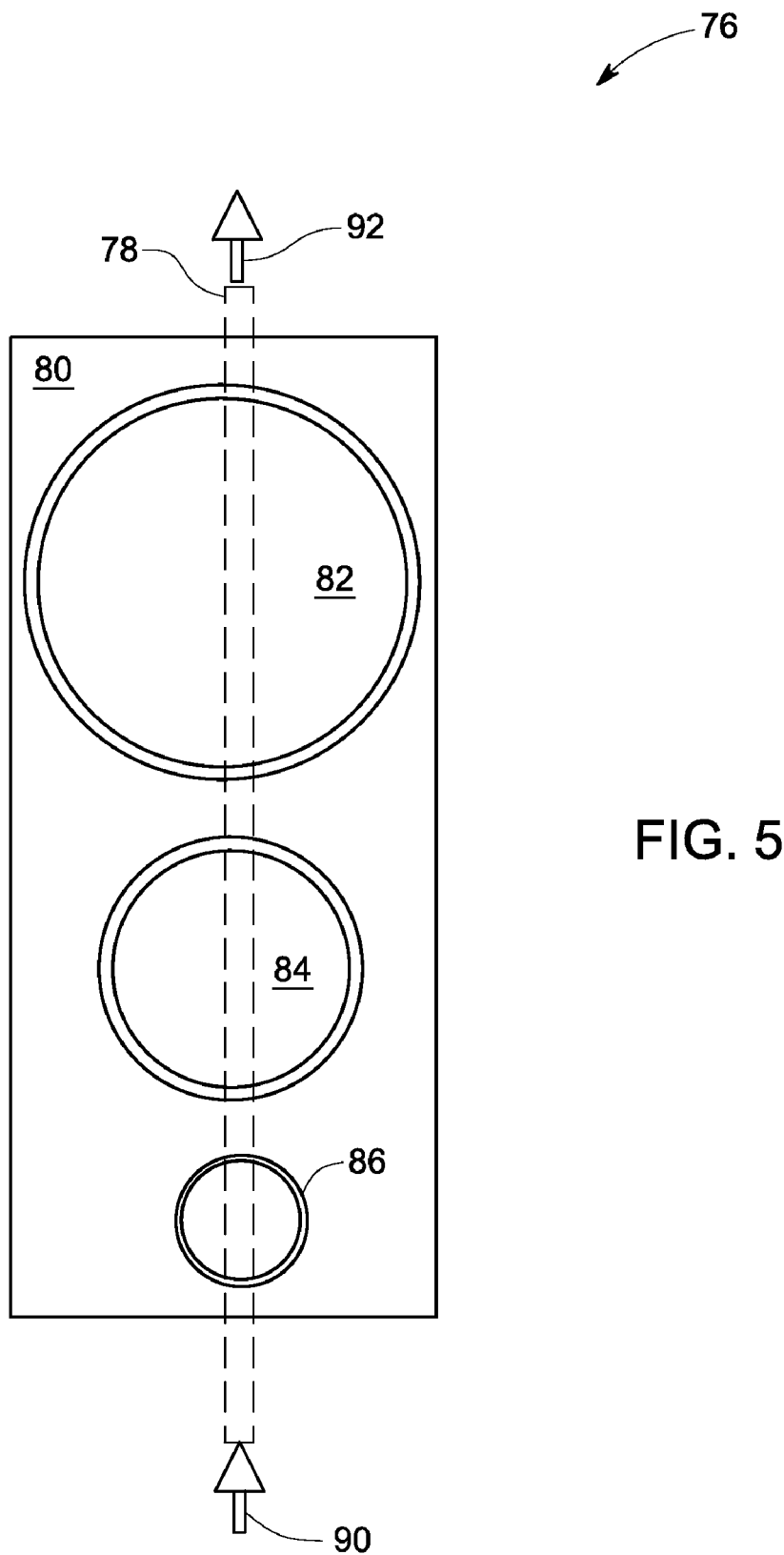
FIG. 5 is a top view of an example of a sensor employing a plurality of microspheres disposed in a holder component in the form of a continuous layer, in accordance with embodiments of the present technique.

FIG. 5 illustrates an example of a sensor 76 employing a waveguide 78, a holder component 80, having cavities for disposing three uniquely sized microspheres 82, 84 and 86. In the illustrated embodiment, the three different microspheres 82, 84 and 86 are shown as being progressively larger in size, however, it should be noted that any other possible distribution of sizes of the microspheres 82, 84 and 86 is also envisioned within the scope of the invention. Also, the number of microspheres employed in the sensor of the present invention may depend on the number of analytes to be detected, or the size of the waveguide 88. Arrows 90 and 92 represent the direction of propagation of light within the waveguide 78.

Note that in embodiments where a plurality of microspheres is employed, nearest neighbor microspheres may interfere with one another, making the overall optical transmission spectrum different from the product of the transmission spectra obtained for individual spheres. Accordingly, the minimum distance between the microspheres is selected to avoid such interferences.

In certain embodiments, the sensor may be disposed in the environment (e.g., a solution) where the analyte is present. In one example, the sensor may be disposed in a solution having the analyte. In another example, the sensor may be simply exposed to the environment. Whether the analyte is present in a liquid medium, or a gaseous medium, typically, a light source is coupled to the waveguide, and the transmission spectrum from the waveguide is analyzed. In the transmission spectrum, the resonance frequencies appear as dips in the transmission spectrum. The shift in the resonance frequency is determined. In one example, the differences between the position of the dips before and after disposing the sensor in the environment (e.g., solution) is calculated. The determined change in resonance frequency (or determined change in the corresponding wavelength) may be used for detection or measurement of the analyte. Optionally, the above steps may be repeated to determine adsorption on other microspheres (in case of employing two or micro spheres).

Figure 6:
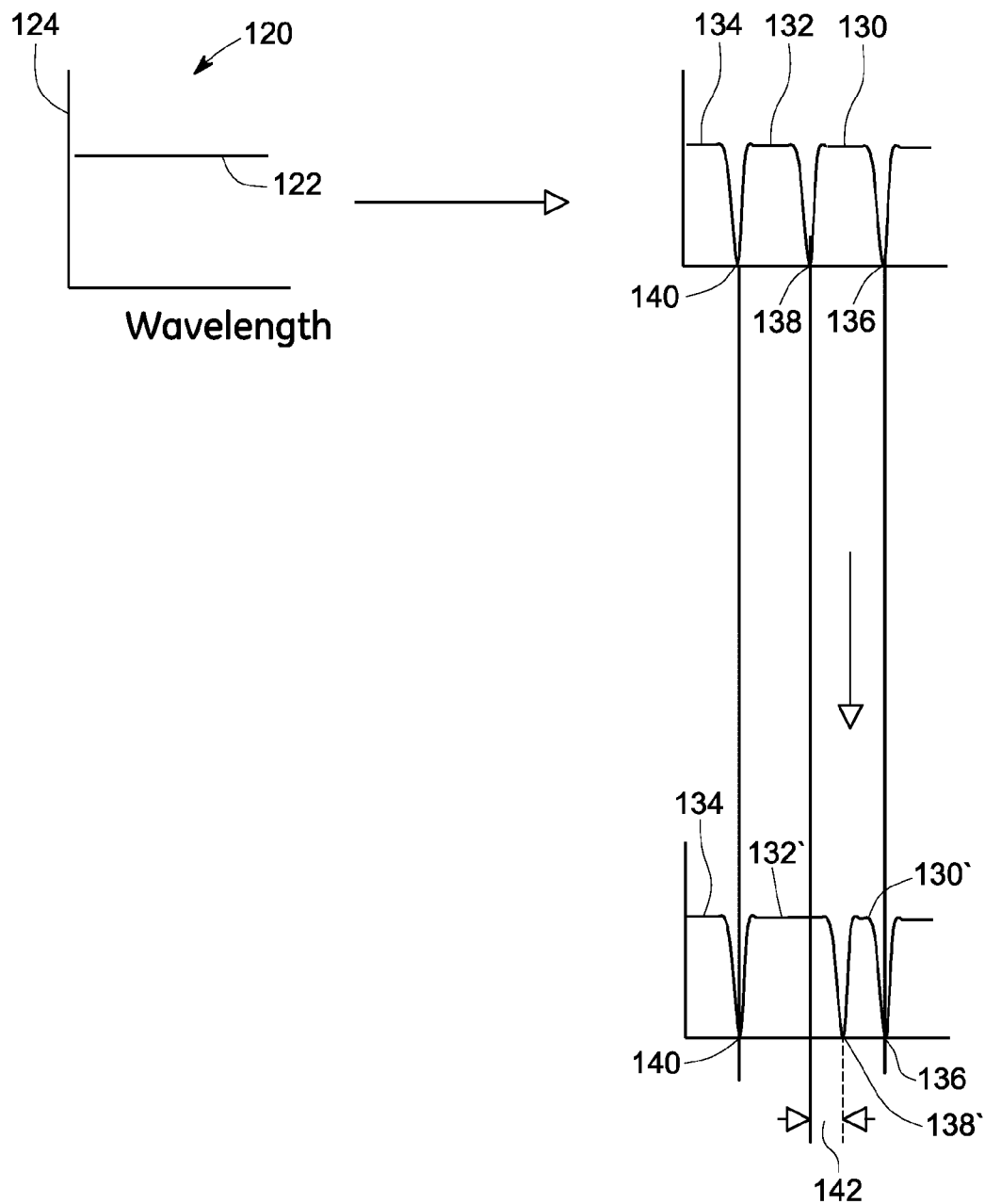
FIG. 6 is a graphical representation of shift in resonance frequency of the microsphere due to analyte binding on one of the microspheres as shown in FIG. 5.

FIG. 6 represents a graph 120 for an input white light 122 having a constant intensity 124 (ordinate 126). Graph 122 indicates output light from the waveguide, such as waveguide 78 (see FIG. 5). Each of the curves 130, 132 and 134 corresponds to different microspheres, such as microspheres 82, 84 and 86 (see FIG. 5), respectively. Each of the microspheres 82, 84 and 86 has corresponding resonance frequencies 136, 138 and 140, respectively. When a binding event takes place on a microsphere, the resonance frequency of that microsphere experiences a shift. In the illustrated example, a binding event occurs at the micro sphere 84, thereby resulting in a shift 142 in the resonance frequency 138' of the microsphere 84. The shift in resonance frequency 138 of the micro sphere 84 is also reflected by change in shape of the curves 130 and 132, to 130' and 132', respectively.

Figure 7:
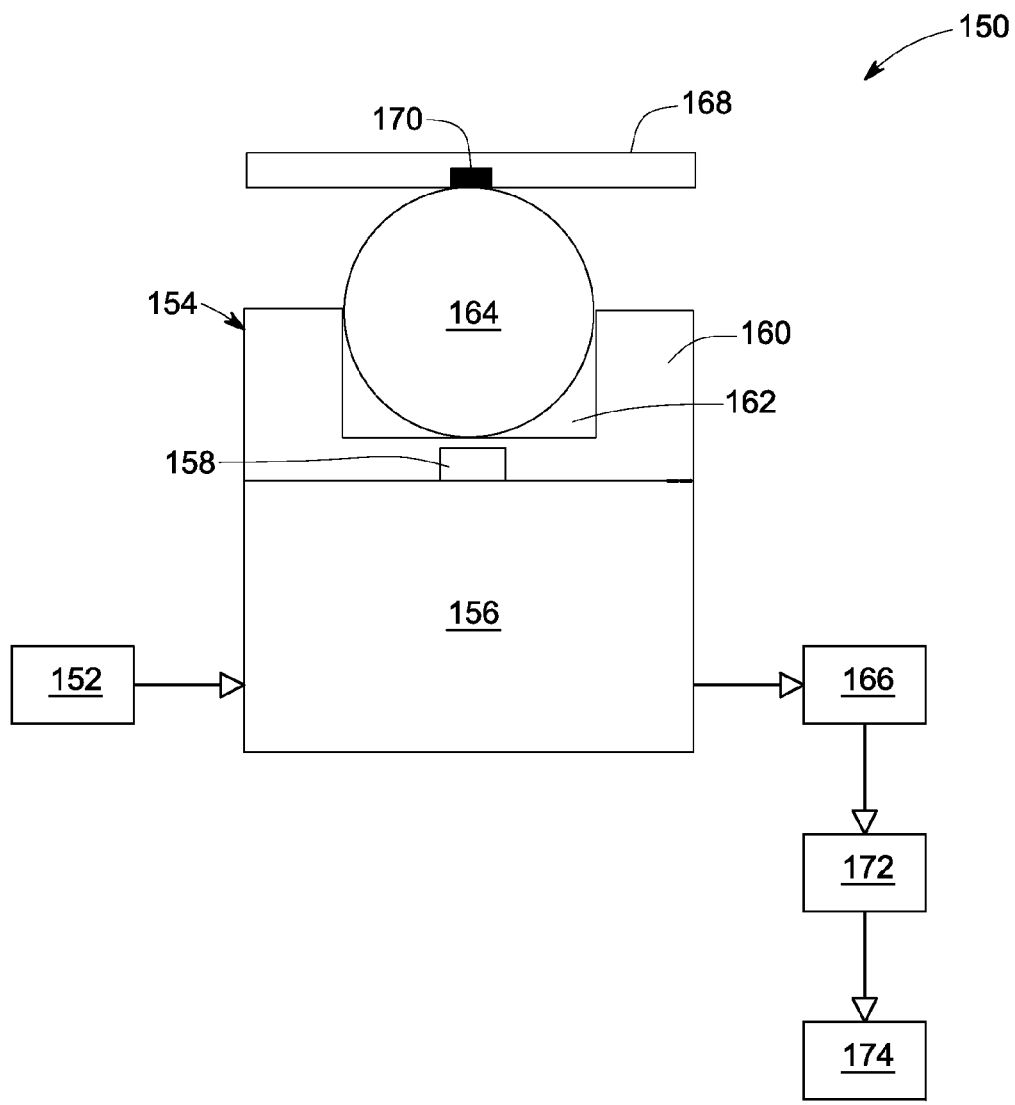
FIG. 7 is a cross-sectional view of an example of an optical sensor system, in accordance with embodiments of the present technique.

FIG. 7 illustrates an example of a sensor system 150 having a light source 152, a sensor 154 to receive illumination from the light source 152. The sensor 154 includes a substrate 156, and a waveguide 158. The sensor 154 further includes a holder component 160 disposed on a portion of the substrate 156, and the waveguide 158. The holder component 160 includes a cavity 162 having a microsphere 164 disposed therein. The transmission spectrum of the waveguide 158 is detected using a detector 166.

In the illustrated embodiment, the sensor system 150 is adapted to detect analyte species present in a liquid solution. Accordingly, the system 152 includes a microfluidic chip 168 having a microfluidic channel 170. The microfluidic channel 170 is employed to transport the analyte solution to the microsphere 164.

In one embodiment, the light source 152 may include a white light source, a tunable laser, or a light emitting diode (LED). In one embodiment, the detector 166 may include a spectrum analyzer, a photodetector, a spectrometer, or a charge coupled device (CCD). The detector 166 may be a photodetector for recording light intensity at various frequencies. In one example, the photodetector may be a photodiode, such as an avalanche photodiode.

Typically, a photodetector may be employed when using monochromatic light, and the spectrometer, or CCD may be employed when using a white light. In embodiments where the detector 166 is a charge-coupled detector (CCD), the detector 166 may record the spectrum of the output light. In one embodiment, the spectrometer is a 2-D spectrometer. The 2-D spectrometer may include a 2-D array of suitable resolution. In case of the sensor system 150 employing a plurality of microspheres, there is a corresponding column or row in the 2-D spectrometer for each of the microspheres in the fluidic chip. By quantifying the shift in the resonance frequency, the concentration of the analytes may be measured. In another embodiment, the detector 166 is a 1-D spectrometer.

The resonant frequencies of the microspheres having the functional material, seen as dips, may be recorded by the detector. The light may be detected by a broadband photodiode detector, for example, which may be coupled to one end of the waveguide. The resonant frequencies may be recorded by the photodetector. In the case of employing two or more microspheres, these resonant frequencies may be associated with the various microspheres. Given that the difference between the diameters of any two micro spheres is at least about 2 percent of the diameters of the smaller microsphere, the resonances from the different microspheres are easily distinguishable.

The detector 166 may be coupled to a detection circuitry (not shown). In one example, the detection circuitry may convert current signal to voltage signal. Also, the detection circuitry may proportionally amplify the signal received from the detector 166. The detection circuitry may include components, such as, but not limited to, data processor, for receiving measurements of shift in resonance frequency from the detector 166, such as a spectrometer, and for conducting analysis thereon.

The detector 166 may be coupled to a data processor 172 for receiving measurements of resonance frequency from the spectrometer and for conducting analysis thereon. The system 150 may also include a display 174, such as a monitor, for displaying the transmission spectrum and/or the analysis results.

A computer may be used to process and display the signals. The computer may be used to generate a variety of quantitative and qualitative measures. In addition, the computer may access a spectrum library, which stores the information regarding the spectral characteristics of various elements or chemical compounds. This spectrum library may be used to identify unknown samples by comparing the spectral information received from an unknown sample with spectral patterns retained in the library, and identification of the unknown substance may be made by comparison.

Figure 8:
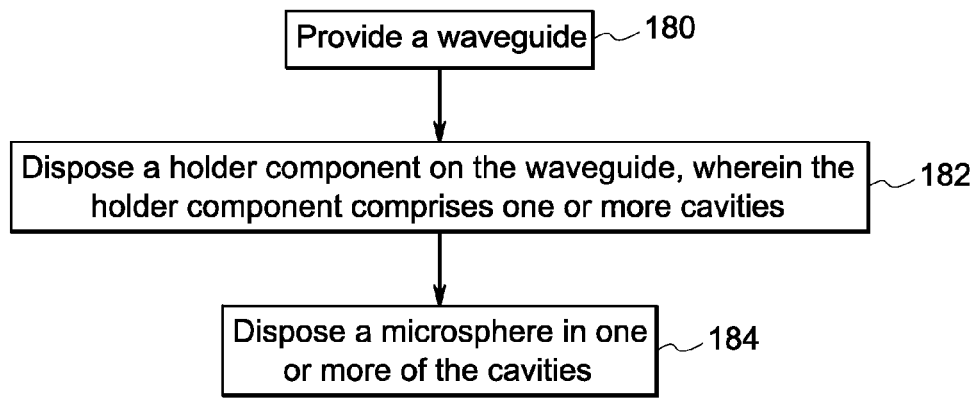
FIG. 8 is a flow chart illustrating an example of various steps involved in the method for making an optical sensor.

Referring now to FIG. 8, a method for making a sensor is provided. The method begins by providing a waveguide disposed on a substrate (block 180). The waveguide may be selected depending on the nature of light (monochromatic, or white light) to be used in the waveguide.

Next, at block 182, a holder component is disposed on at least a portion of the substrate, or the waveguide, or both. The holder component includes at least one cavity. In one embodiment, the holder component being disposed on the waveguide may already have a cavity. In another embodiment, the cavity is formed in the holder component after disposing the holder component on the substrate and/or the waveguide. In this embodiment, a thin film may be deposited on the substrate and/or the waveguide, and subsequently, cavities are formed on the thin film. The cavities may be formed using techniques, such as dry etching, wet etching, or lithography, such as photolithography.

Subsequent to forming the cavities, a microsphere is disposed in the cavity of the holder component (block 184). In certain embodiments, disposing the microspheres in the cavity includes functionalizing at least one microsphere. In one embodiment, the plurality of microspheres may be functionalized using same or different functional materials. The functionalized microspheres may be disposed on the holder component. In one example, the holder component may be spun at a determined frequency/rpm to enable the microspheres to become situated in the cavities.

Figure 9:
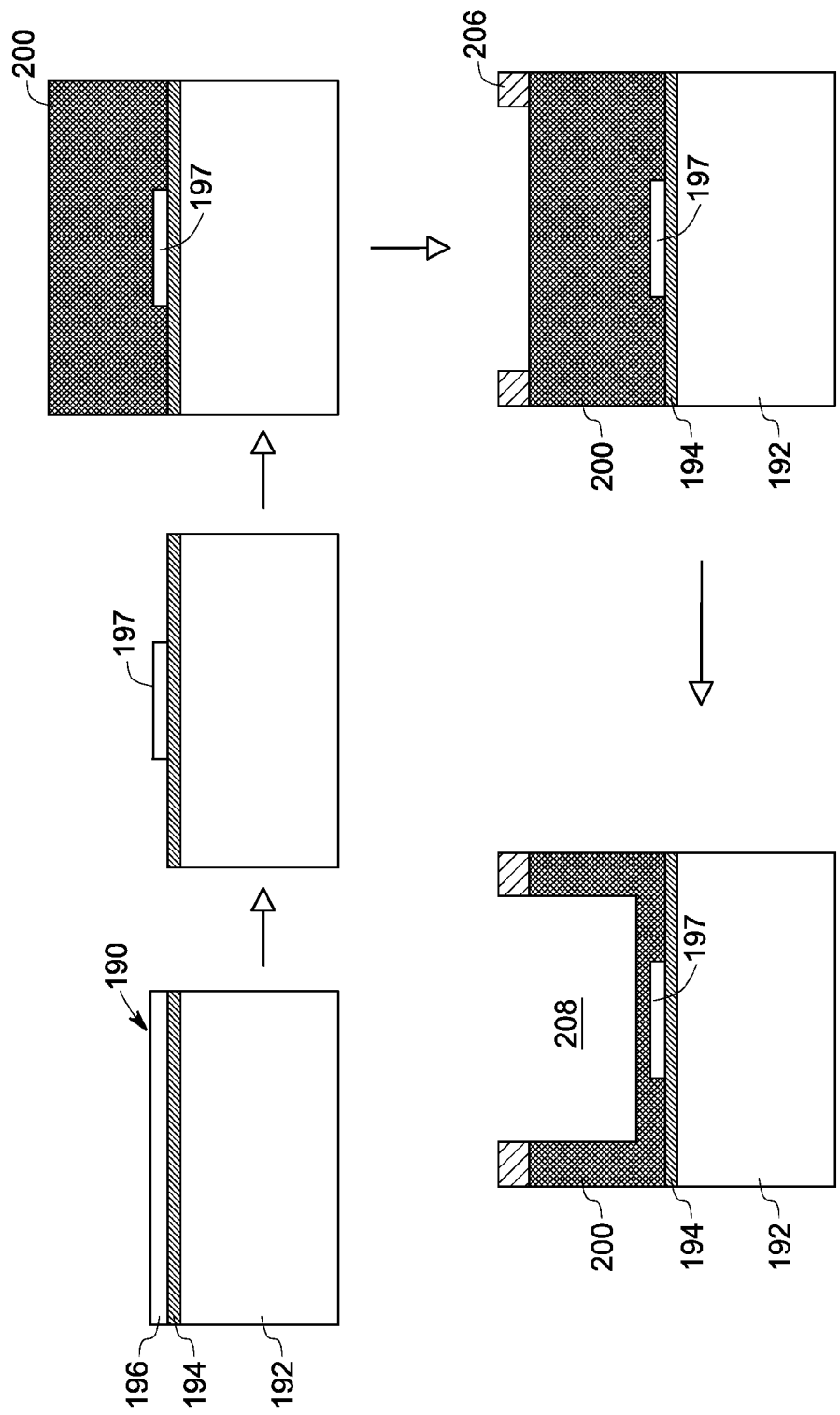
FIGS. 9-10 are schematic representations of the various steps involved in the method of making an optical sensor, in accordance with embodiments of the present technique.

FIG. 9 illustrates detailed steps for method of making the sensor in accordance with one embodiment. A SOI wafer 190 is provided. The SOI wafer 190 includes a bulk silicon wafer 192, an insulator layer 194, and a silicon layer 196 disposed on the insulator layer 194. A waveguide 197 is formed by etching a portion of the silicon layer 196. Although not illustrated, subsequent to etching, the etched portion 197 is patterned on the inner side using techniques, such as but not limited to, photolithography to form the waveguide.

A thin film 200 is disposed on the insulator layer 194 and the waveguide 197. The thin film may be deposited using techniques such as, but not limited to, spin coating, chemical vapor deposition (CVD), physical vapor deposition, plasma enhanced chemical vapor deposition (PECVD), sputtering, or molecular beam epitaxy (MBE). In one embodiment, the thickness of the thin film 200 may be in a range from about 500 nanometers to about 500 microns.

Columns 206 of photoresist material may be formed using techniques, such as but not limited to, photolithography. In one example, a continuous layer of the photoresist material may be deposited on the thin film 200. Subsequently, a portion of the continuous layer may be etched away to define the columns 206. Etching is then carried out to define the cavity 208. Subsequently, the photoresist columns 206 are removed.

Figure 10:
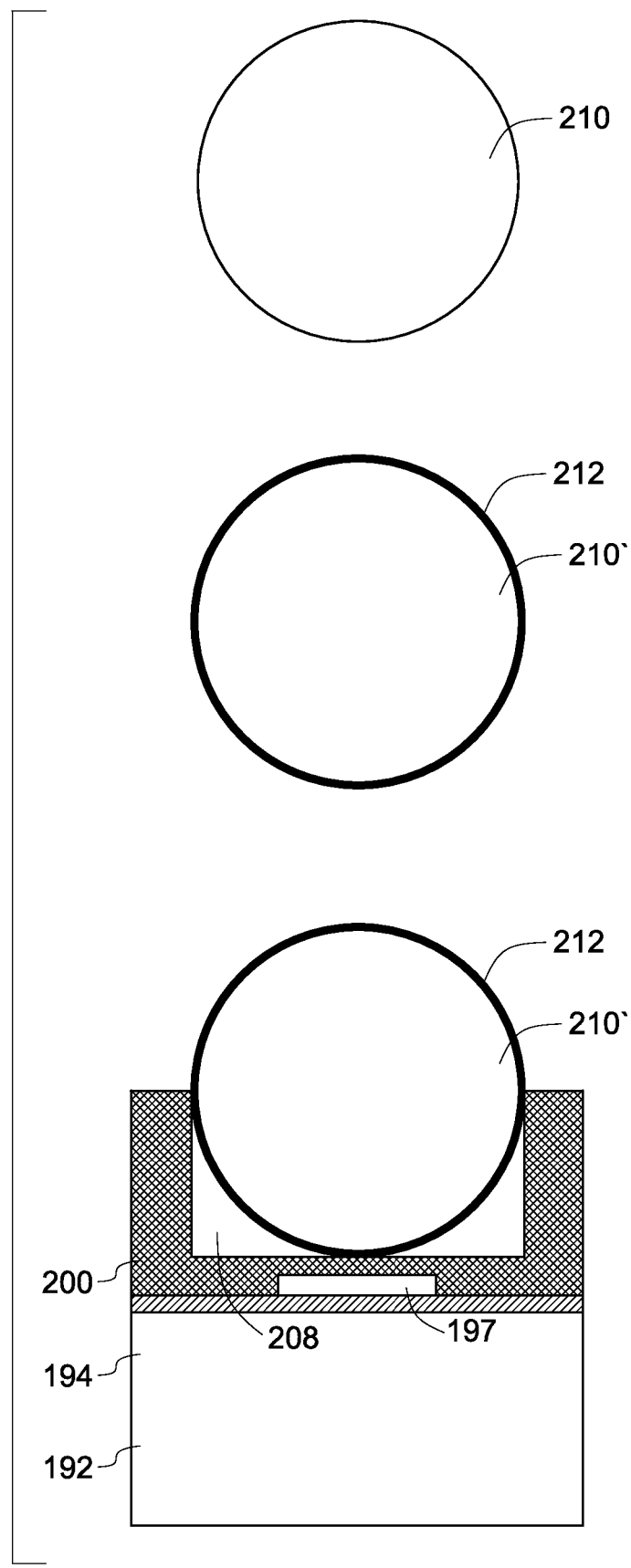

FIG. 10 illustrates steps for functionalizing a microsphere 210 and disposing the functionalized microsphere 210' in the cavity. The microsphere 210 may be functionalized by exposing the microsphere 210 to one or more functional materials. In one embodiment, the microsphere may be disposed in a solution of the functional material. In the illustrated embodiment, the functional material is deposited on the surface of the microsphere 210 in the form of a layer 212. In one example, prior to disposing the functional material on the microsphere 210, the microsphere 210 may be coated with a binding agent, for example an epoxy solution. The coated microsphere may be placed in a solution of functional material, such as amines.

Next, an optional drying step may be carried out. For example, the microsphere 210' may be exposed to a radiation, such as ultraviolet (UV). In embodiments, where a binding agent is used, the radiation causes a reaction between the binding agent and the functional material to form a functionalized micro sphere 210'. The functionalized microsphere 210' includes one or more receptor sites (for analytes) on the surface.

The systems and methods employ simple and robust geometry with simple and robust signal processing, and provide an ability to measure two or more analytes in a same or different environment (such as analyte solution). In addition, advantageously, the present technique employs a "label-free" approach, which does not require chemical tagging of the target molecules for detection. Accordingly, the system not only reduces number of operations, but also reduces measurement artifacts by reducing complexity. The systems and methods allow the target molecules to be studied/analyzed in the natural state without additional labels.

In addition, the arrangement of the system may be made portable if applications in the field are necessary because the device can be miniaturized. The sensor and sensor systems disclosed herein could be also manufactured with low cost using IC manufacturing foundry.

Simply disposing the microsphere within the cavity is sufficient to align the micro sphere with the waveguide to enable optical coupling between the two. This simple approach to optical coupling contributes to making a robust sensor that is easy to handle and use. Once the microsphere is disposed in the cavity, no additional alignment steps are required, thereby simplifying the fabrication of the sensor. Also, the number of microspheres can be increased without increasing the system complexity. Thus, multi-channel detection, and high throughput may be achieved using the sensor of the present technique.

The sensor may be used in diagnosis of infectious disease, point-of-care (POC) testing, and biological security. The sensors of the present invention may be used in low-resource settings, such as for home healthcare applications or as portable, field instruments. The sensors are highly sensitive, miniaturized, optical-sensing component that allows detection of single pathogens or disease biomarkers without the need for amplification or labeling of the molecules.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensor, comprising:
   a substrate;
   a waveguide having a first surface and a second surface disposed opposite to the first surface, wherein the waveguide is disposed on the substrate such that at least a portion of the second surface of the waveguide is in physical contact with the substrate;
   a holder component disposed on at least a portion of the substrate, or the waveguide, or both, wherein the holder component comprises one or more cavities; and
   at least one microsphere at least partially disposed in a corresponding cavity of the holder component, wherein the first surface of the waveguide and the at least one microsphere are spaced apart from each other to define a gap.

2. The sensor of claim 1, wherein the waveguide comprises a single mode waveguide, a multiple mode waveguide, a rectangular waveguide, or a slot waveguide.

3. The sensor of claim 1, wherein the holder component comprises a patterned continuous layer.

4. The sensor of claim 1, wherein the holder component comprises a plurality of discrete portions comprising one or more cavities.

5. The sensor of claim 1, wherein a thickness of a portion of the holder component disposed between the first surface of the waveguide and the microsphere is in a range from about 0 microns to about 2 microns.

6. The sensor of claim 1, wherein the holder component comprises a plastic, glass, a dielectric material, a thermally or ultraviolet curable polymer, or combinations thereof.

7. The sensor of claim 1, wherein the gap comprises air, nitrogen, an inert gas, or combinations thereof.

8. The sensor of claim 1, wherein the waveguide comprises an inorganic glass, silicon, a III-V compound semiconductor, a II-VI compound semiconductor, a polymer, or combinations thereof.

9. The sensor of claim 1, wherein the microsphere comprises silicon, silica, sapphire, a polystyrene, a poly(methyl methacrylate), a polycarbonate, a poly(ethylene terephthalate), or combinations thereof.

10. The sensor of claim 1, further comprising a modifier material disposed on at least one microsphere.

11. The sensor of claim 10, wherein the modifier material comprises a dielectric material, glass, silicon, or combinations thereof.

12. The sensor of claim 1, further comprising a functional material disposed on at least one microsphere.

13. The sensor of claim 1, comprising a plurality of uniquely sized micro spheres.

14. The sensor of claim 13, wherein a difference in diameters of any two microspheres is at least about two percent of the diameter of the smaller microsphere.

15. A sensor system, comprising:
    a light source;
    a sensor disposed to receive illumination from the light source, the sensor comprising:
      a substrate;
      a waveguide having a first surface and a second surface disposed opposite to the first surface, wherein the waveguide is disposed on the substrate such that at least a portion of the second surface of the waveguide is in physical contact with the substrate;
      a holder component disposed on at least a portion of the substrate, or the waveguide, or both, wherein the holder component comprises one or more cavities;
      at least one micro sphere at least partially disposed in a corresponding cavity of the holder component, wherein the first surface of the waveguide and the at least one micro sphere are spaced apart from each other to define a gap; and
    a detector that detects a shift in a resonance wavelength of one or more micro spheres.

16. The sensor system of claim 15, wherein the light source comprises a white light source, a tunable laser, or a light emitting diode (LED).

17. The sensor system of claim 15, wherein the detector comprises a spectrum analyzer, a photodetector, a spectrometer, or a charge coupled device.

18. The sensor system of claim 15, further comprising microfluidic channels coupled to at least one microsphere.

19. A method for making a sensor, comprising:
providing a waveguide disposed on a substrate, wherein the waveguide comprises a first surface and a second surface disposed opposite to the first surface, wherein the waveguide is disposed on the substrate such that at least a portion of the second surface of the waveguide is in physical contact with the substrate;
disposing a holder component on at least a portion of the substrate, or the waveguide, or both, wherein the holder component comprises at least one cavity; and
disposing at least one microsphere in the at least one cavity of the holder component such that the first surface of the waveguide and the at least one microsphere are spaced apart from each other to define a gap.

20. The method of claim 19, wherein disposing the holder component comprises:
depositing a thin film on at least a portion of the substrate, or the waveguide, or both; and
forming at least one cavity in the thin film.

21. The method of claim 19, wherein disposing the microspheres comprises:
functionalizing at least one microsphere,
disposing the at least one functionalized microsphere on the holder component; and
spinning the substrate.

* * * * *